United States Patent [19]

Green

[11] Patent Number: 4,557,263
[45] Date of Patent: Dec. 10, 1985

[54] APPARATUS FOR APPLYING SURGICAL CLIPS

[75] Inventor: David T. Green, Norwalk, Conn.

[73] Assignee: United States Surgical Corporation, Norwalk, Conn.

[21] Appl. No.: 573,154

[22] Filed: Jan. 23, 1984

[51] Int. Cl.⁴ ............................................. A61B 17/12
[52] U.S. Cl. .................................. 128/325; 206/339; 221/197; 227/DIG. 1
[58] Field of Search ......................... 128/325–327; 221/197, 198; 227/DIG. 1, DIG. 1 A, DIG. 1 B, DIG. 1 C; 206/339

[56] References Cited

U.S. PATENT DOCUMENTS

| 1,199,653 | 9/1916 | Bacolini. | |
|---|---|---|---|
| 1,203,269 | 10/1916 | Richter. | |
| 2,090,831 | 8/1937 | Burkhardt | 1/49.1 |
| 2,194,748 | 3/1940 | Glaser | 81/3 |
| 2,237,589 | 4/1941 | Dole | 1/56 |
| 2,277,139 | 3/1942 | Niemand | 227/DIG. 1 |
| 2,594,102 | 4/1952 | Vollmer | 1/49.1 |
| 2,733,441 | 2/1956 | White | 1/49.1 |
| 2,744,251 | 5/1956 | Vollmer | 1/49.1 |
| 2,968,041 | 1/1961 | Skold | 1/49.1 |
| 3,047,874 | 8/1962 | Kelsey | 1/349 |
| 3,086,208 | 4/1963 | Eby | 1/56 |
| 3,110,899 | 11/1963 | Warren | 1/349 |
| 3,152,336 | 10/1964 | Brady | 1/349 |
| 3,234,636 | 2/1966 | Brown | 29/212 |
| 3,518,993 | 7/1970 | Blake | 128/321 |
| 3,646,801 | 3/1972 | Caroli | 72/410 |
| 3,775,826 | 12/1973 | Reed | 29/212 |
| 3,777,538 | 12/1973 | Weatherly | 72/410 |
| 3,882,854 | 5/1975 | Hulka | 128/6 |
| 4,027,510 | 6/1977 | Hiltebrandt | 72/37 |
| 4,152,920 | 5/1979 | Green | 72/410 |
| 4,166,466 | 9/1979 | Jarvik | 128/325 |
| 4,201,314 | 5/1980 | Samuels et al. | 221/198 |
| 4,202,480 | 5/1980 | Annett | 227/DIG. 1 |
| 4,226,242 | 10/1980 | Jarvik | 128/325 |
| 4,242,902 | 1/1981 | Green | 72/410 |
| 4,246,903 | 1/1981 | Larkin | 128/325 |
| 4,296,751 | 10/1981 | Blake | 128/325 |
| 4,299,224 | 11/1981 | Noiles | 128/325 |
| 4,316,468 | 4/1982 | Klieman | 128/325 |
| 4,412,539 | 11/1983 | Jarvik | 128/325 |
| 4,425,915 | 1/1984 | Ivanov | 128/325 |
| 4,427,008 | 1/1984 | Transue | 128/325 |
| 4,430,997 | 2/1984 | DiGiovanni | 128/326 |
| 4,452,376 | 6/1984 | Klieman et al. | 128/325 |
| 4,471,780 | 9/1984 | Menges et al. | 227/DIG. 1 |
| 4,491,133 | 1/1985 | Menges et al. | 128/326 |
| 4,492,232 | 1/1985 | Green | 227/DIG. 1 |

FOREIGN PATENT DOCUMENTS

| 1098483 | 2/1983 | Australia. |
| 1098583 | 2/1983 | Australia. |
| 1098683 | 2/1983 | Australia. |
| 2074030 | 10/1981 | United Kingdom. |
| 2074031 | 10/1981 | United Kingdom. |

Primary Examiner—Andrew H. Metz
Assistant Examiner—Terryence Chapman
Attorney, Agent, or Firm—John E. Nathan; Robert R. Jackson; Alan M. Gordon

[57] ABSTRACT

Surgical clip applying apparatus for advancing and closing clips one at a time around body tissue. The apparatus includes a cartridge with a carrier member for an array of clips. When the cartridge is moved distally relative to the apparatus, two pivotally mounted cam followers on the carrier member move toward each other and traverse a pair of jaws on the apparatus. The pivoting of the cam followers causes the distalmost clip to be closed around body tissue. The cam followers and the cartridge then return to their original positions to ready the apparatus for another cycle of operation.

31 Claims, 11 Drawing Figures

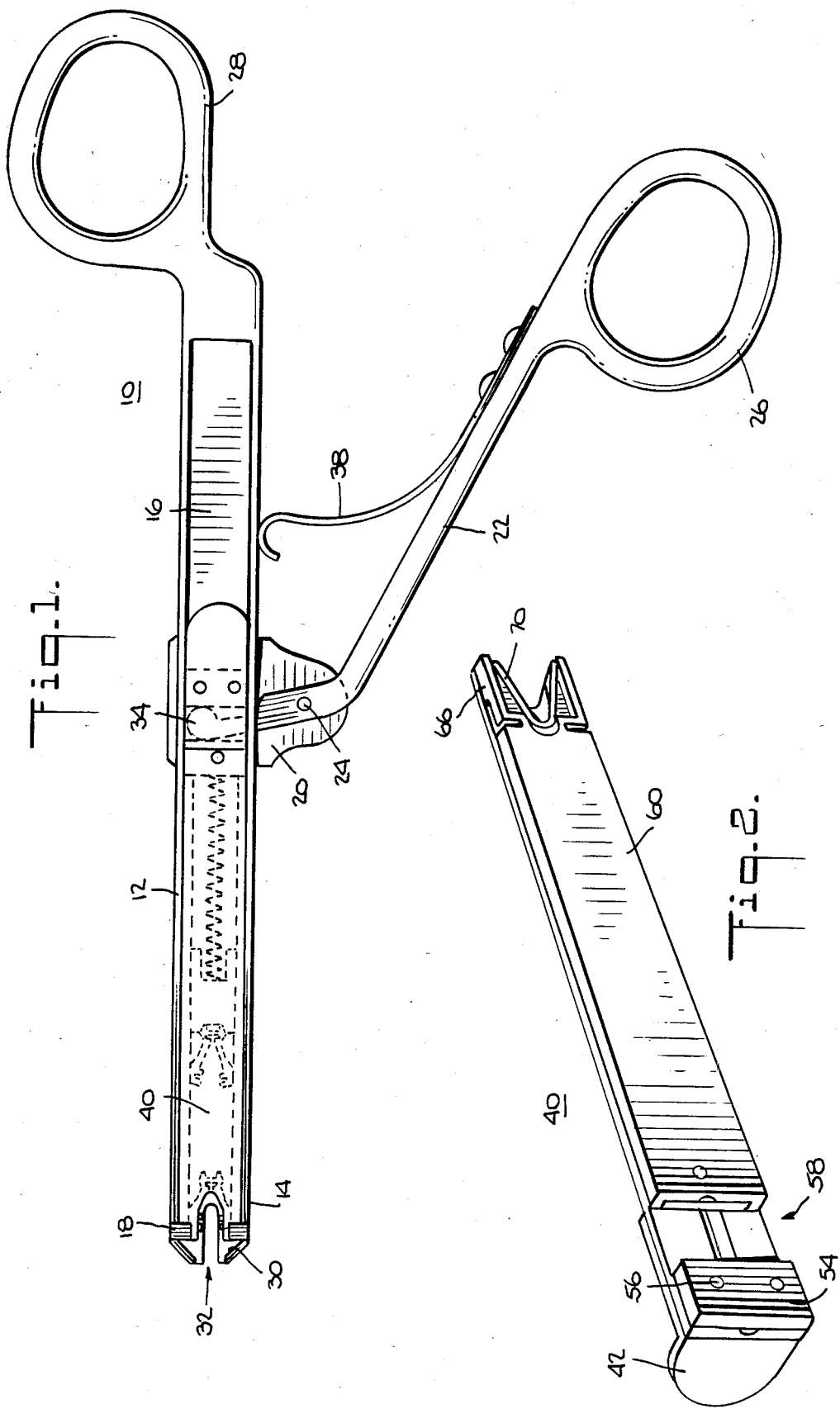

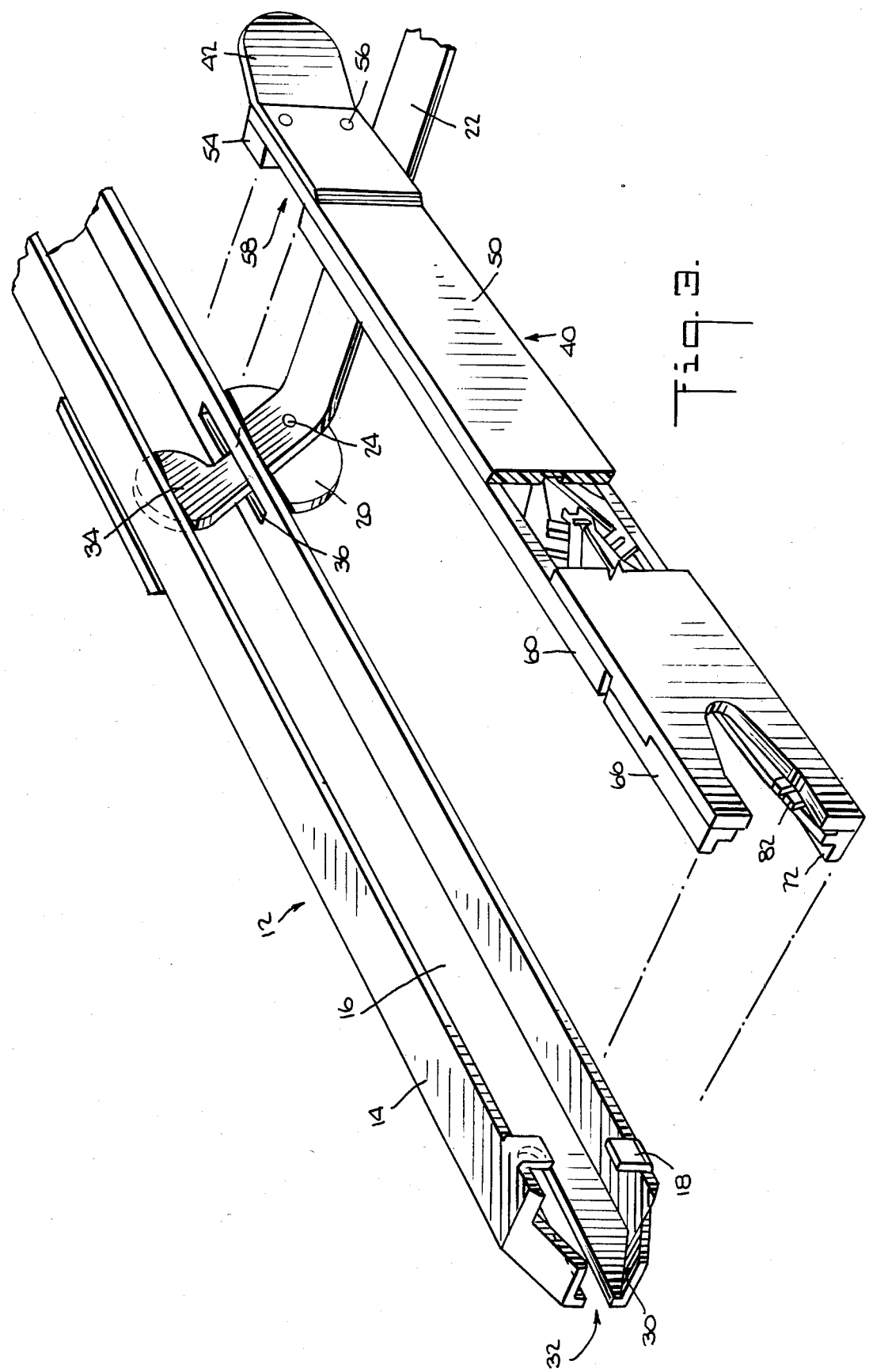

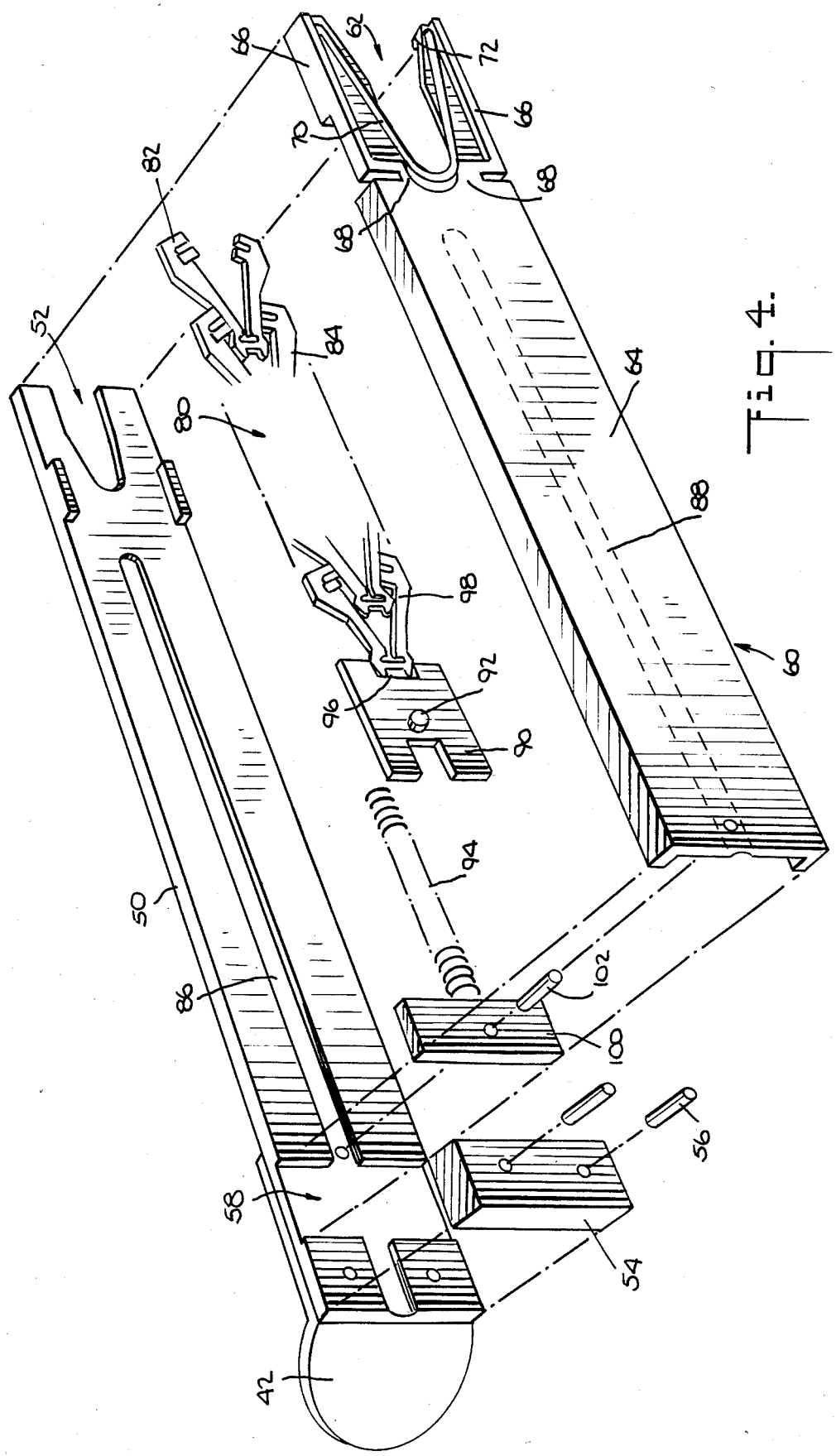

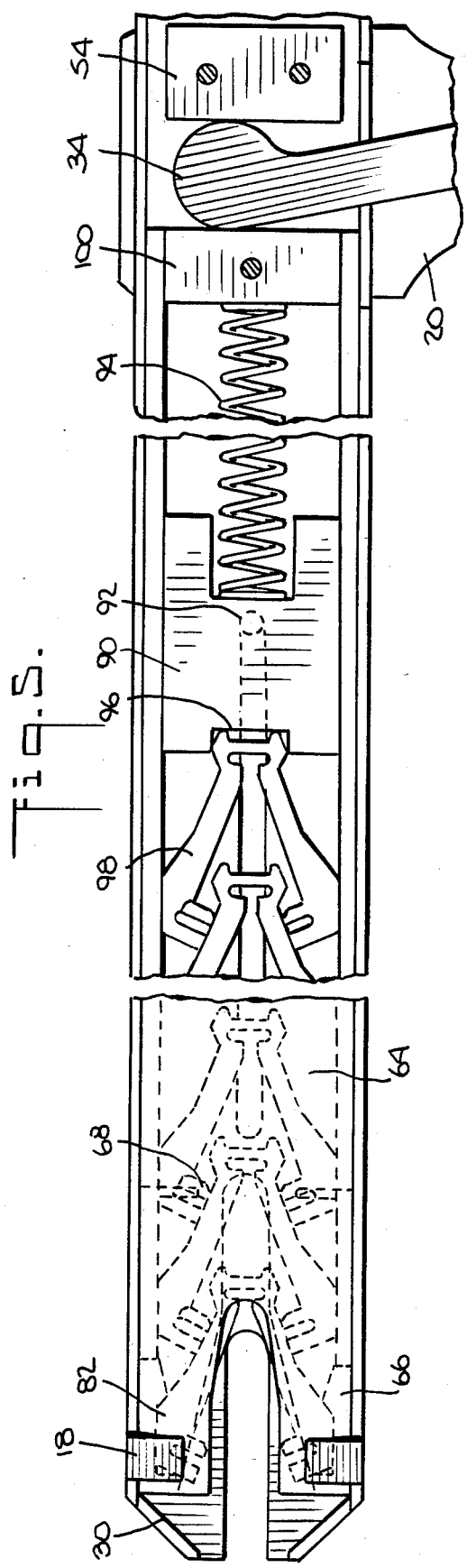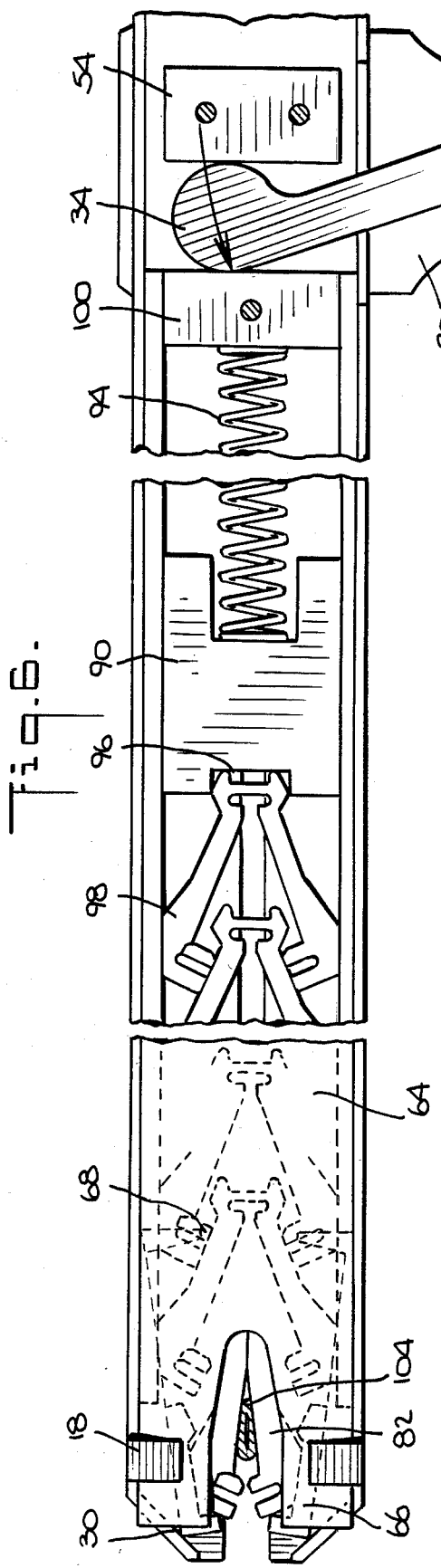

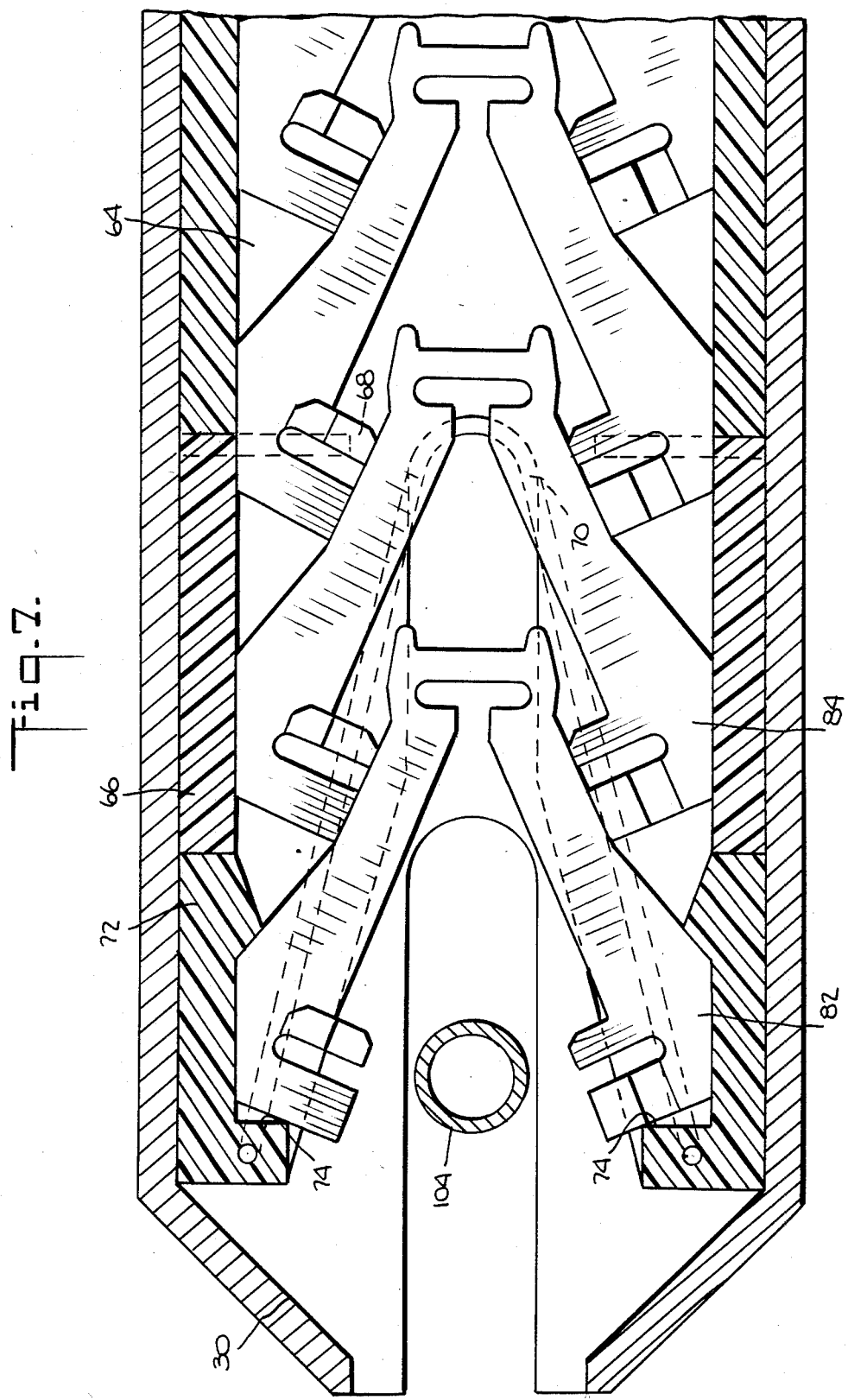

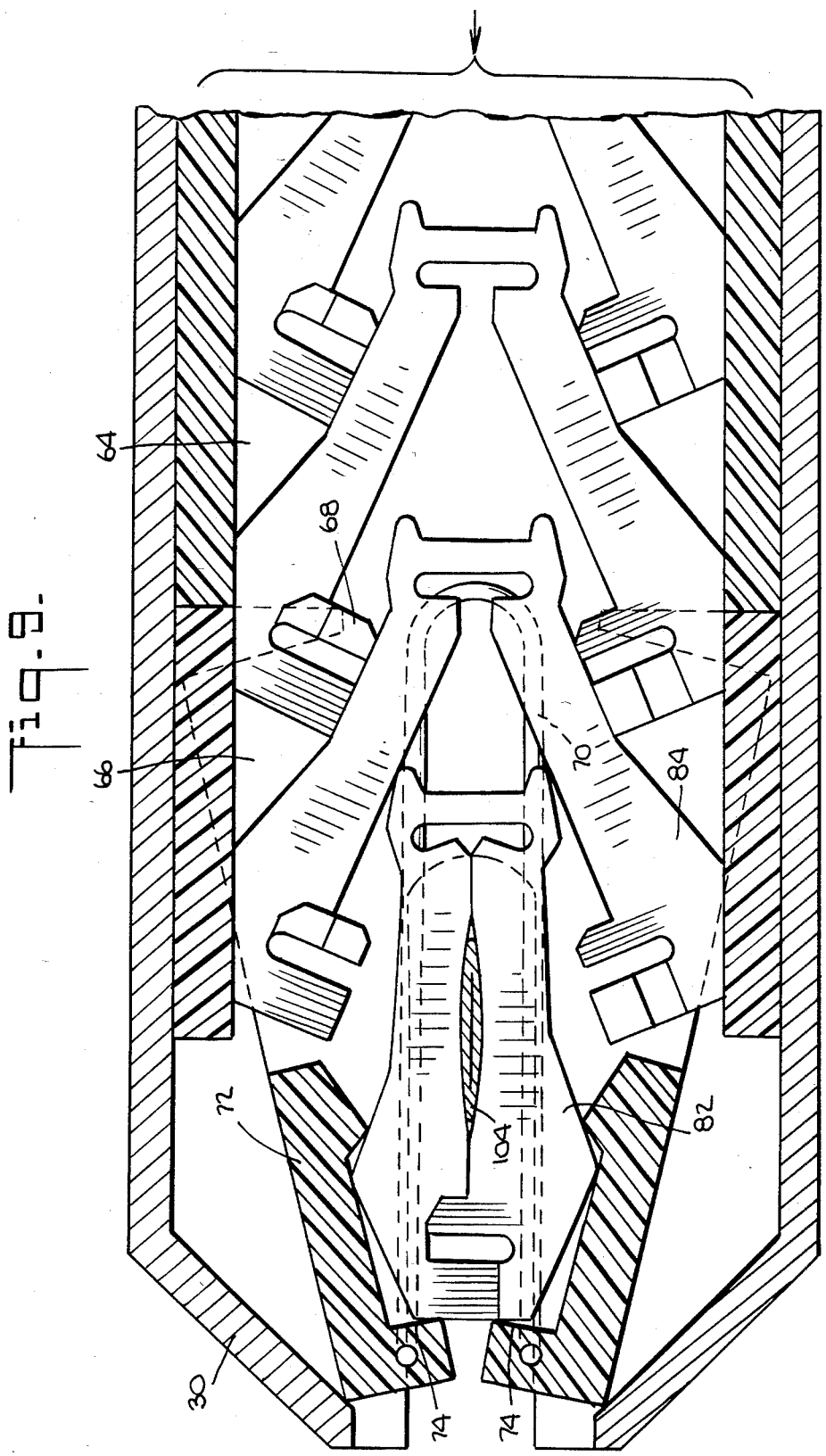

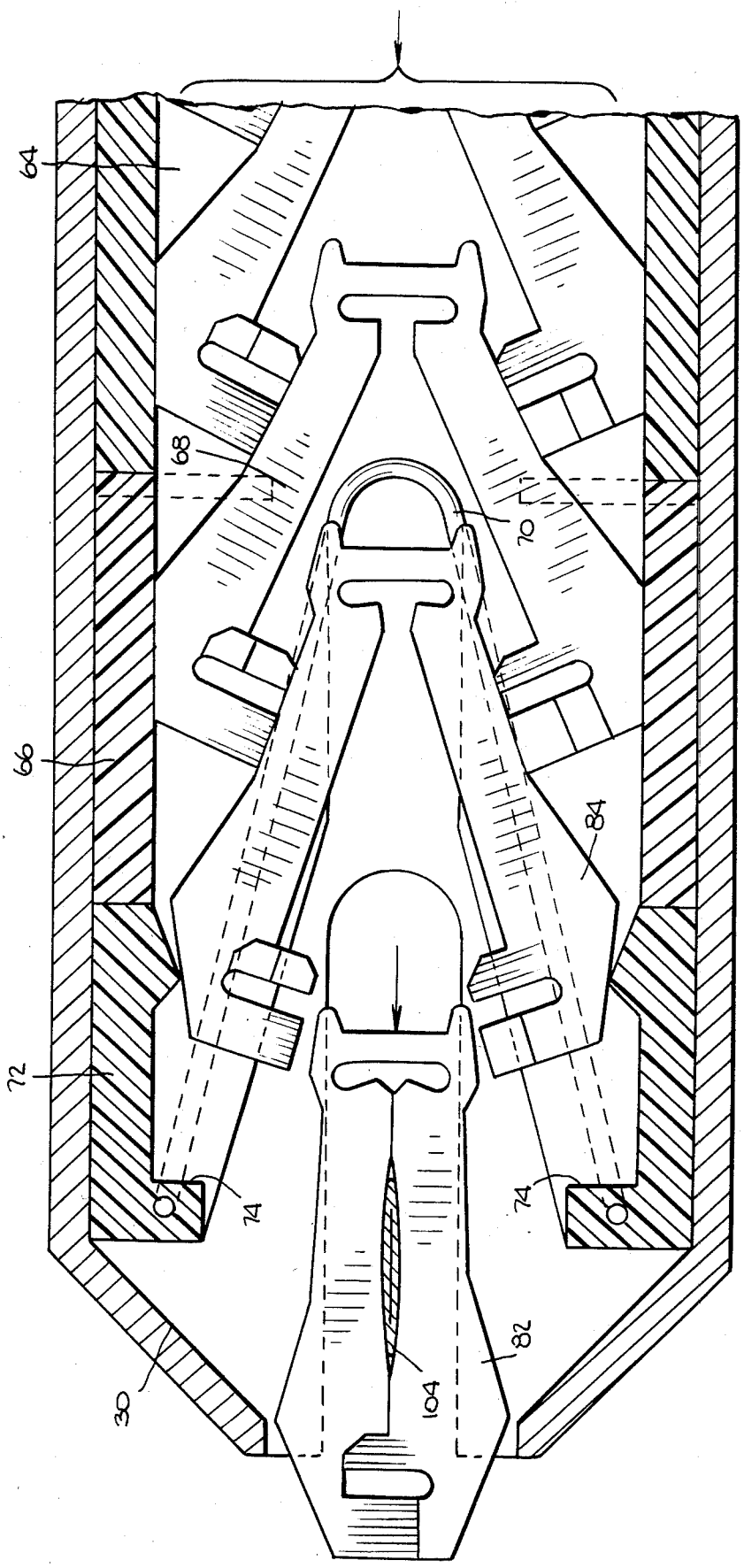

4,557,263

APPARATUS FOR APPLYING SURGICAL CLIPS

BACKGROUND OF THE INVENTION

This invention relates to apparatus for applying surgical clips to body tissue, and more particularly to clip appliers of the type which are used to apply a surgical clip to a tubular body structure. An example is the application of a clip to the vas deferens in order to perform a vasectomy.

Surgical clip appliers typically have a pair of laterally spaced, relatively movable jaws for receiving a clip to be applied to body tissue. After the jaws receive a clip, the jaws are brought together to close the clip around the tissue. A variety of methods have been employed for bringing the jaws together, including the use of a pliers-type actuator, a sleeve which interacts with the jaws to cam them closed, and direct manual pressure on the jaws. This last method is the most cumbersome and unreliable, due to the need for two-handed operation which makes the application of a clip difficult in confined working areas of the body.

Some surgical clip appliers have an element which supports an array of clips. In the prior art, this element does not function in any way to effect the camming of the jaws to close a clip around the tissue. The use of separate elements to support clips and to close clips necessarily results in instruments that are complex in construction. This tends to make the instruments bulkier, thereby possibly interfering with the operator's view of the jaws during the closing of the clips. This can be a major disadvantage in delicate surgical procedures. In addition, bulkier instruments increase the distance from the operator's hand to the clip application site, which may reduce the accuracy in placing the clips.

In view of the foregoing, it is an object of this invention to improve and simplify surgical clip applying apparatus.

It is a more particular object of this invention to provide surgical clip applying apparatus in which a single element functions both as a clip carrier and a clip closing means.

SUMMARY OF THE INVENTION

These and other objects of the invention are accomplished in accordance with the principles of the invention by the use of a carrier member for clips which also includes two pivotally mounted cam followers which are movable toward each other to close a surgical clip around a tubular body structure.

The clip carrier may be formed as part of a disposable cartridge or clip holder, which in turn is placed in a surgical instrument. Alternatively, the entire instrument/cartridge assembly may be made (1) permanent and reloadable or (2) disposable. The instrument contains means to advance the cartridge distally relative to the instrument. As the cartridge moves distally, the clip carrier cam followers contact two laterally spaced cam surfaces on the instrument which are inclined toward each other in the distal direction. The cam followers on the clip carrier pivot toward one another by means of a flexural hinge when contact is made with the instrument cam surfaces.

The cartridge comes assembled with a linear array of surgical clips. The distal-most clip is pre-positioned so as to be retained between the cam follower members. The pivoting of the cam followers causes the distal-most clip to be closed around the tubular body structure. Means are provided to advance the linear array of clips. Stop surfaces are used to prevent the premature advancement to the clip closing position of the next-to-distal-most clip.

This design eliminates the need for separate elements to carry and to close surgical clips. This enables the apparatus to be made smaller, thereby improving access to and visibility of the clip application site.

Further features of the invention, its nature and various advantages will be more apparent from the accompanying drawing and the following detailed description of the invention.

BRIEF DESCRIPTION OF THE DRAWINGS

FIG. 1 is a top plan view of a clip applier.

FIG. 2 is a perspective view of the bottom of the clip-holding part of the clip applier.

FIG. 3 is an exploded perspective view of a portion of the clip applier.

FIG. 4 is an exploded perspective view of the part shown in FIG. 2.

FIG. 5 is a plan view of part of the clip applier with a portion of the top body part cut away. The clip applier is shown at the initial position of the clip-closing cycle.

FIG. 7 is an enlarged view of a portion of the apparatus shown in FIG. 5. The clip applier is shown at the initial position of the clip-closing cycle.

FIG. 8 is a view similar to FIG. 7 except that an intermediate clip-closing position is shown.

FIG. 9 is a view similar to FIG. 7 except that the peak clip-closing position is shown.

FIG. 11 is a view similar to FIG. 7 except that full retraction from the peak clip-closing position to nearly the initial position of the clip-closing cycle is shown.

DETAILED DESCRIPTION OF THE INVENTION

Figure 6:
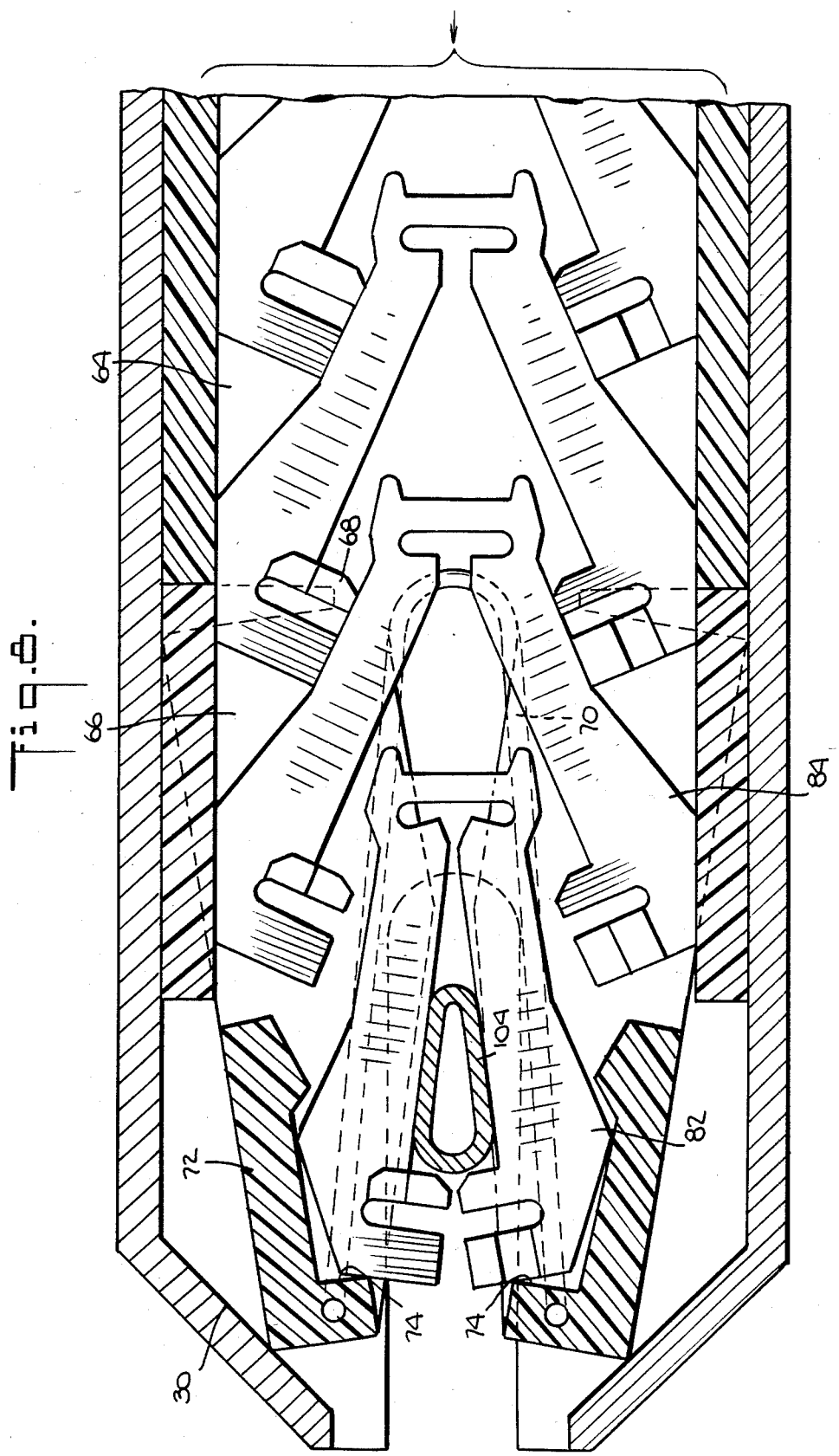
FIG. 6 is a view similar to FIG. 5 except that an intermediate clip-closing position is shown.

Although this invention is also applicable to other embodiments, such as surgical clip appliers which are totally disposable after the initial supply of clips is exhausted, the invention will be fully understood from an explanation of its application to permanent, reusable clip appliers used with disposable clip-holding cartridges which can be replaced after the initial supply of clips is exhausted.

FIGS. 1 and 3 show illustrative clip applier 10 and cartridge 40. Clip applier 10 includes a longitudinal jaw 12 having a distal portion 14. Longitudinal jaw 12 contains a channel 16 to receive cartridge 40, which will be described in detail below. The distal portion 14 of the jaw has two projections 18 which are parallel to and spaced from channel 16 and which serve to retain cartridge 40 within channel 16.

Flange 20 extends from the mid-region of longitudinal jaw 12. Trigger 22 is pivotally attached to flange 20 by means of pivot pin 24. Trigger 22 terminates at its proximal end in a ring handle 26. The proximal portion of longitudinal jaw 12 terminates in another ring handle 28.

The distal portion 14 of longitudinal jaw 12 terminates in a pair of laterally spaced cam surface portions 30 which are inclined toward each other in the distal direction. There is a slot 32 between cam surface portions 30 for admitting the body tissue to be clipped between the cam surface portions.

As will be described in greater detail with reference to FIGS. 5–11, the tissue to be clipped is inserted in slot 32 between cam surfaces 30. The operator grips ring handles 26 and 28 and squeezes them toward one another. This causes trigger 22 to pivot about pivot pin 24, thereby moving the distal force-transmitting portion 34 of trigger 22 in the distal direction. The force-transmitting portion 34 of trigger 22 extends through aperture 36 in longitudinal jaw 12 into channel 16 where it fits in slot 58 in cartridge 40. The above-described distal motion of force-transmitting portion 34 drives cartridge 40 in the distal direction until it contacts cam surfaces 30. As will be described in more detail below, this causes a clip to be closed around the body tissue in slot 32. When the squeezing pressure on ring handles 26 and 28 is relaxed, instrument return spring 38 pivots trigger 22 away from instrument jaw 12, thereby restoring ring handles 26 and 28, trigger 22, and cartridge 40 to their original positions. The clip applier is then removed from around the clipped body tissue, and is ready to apply another clip.

It is to be understood that the invention is not limited to this specific clip applier construction. Rather, any construction is suitable if it reciprocally moves the cartridge in a longitudinal direction against jaw cam surfaces.

FIG. 2 is an overall view of cartridge 40. The cartridge body may be constructed of plastic or other inexpensive materials to facilitate the disposability of the cartridge. The specific details of the cartridge construction are illustrated in FIGS. 3 and 4.

Cartridge 40 has an elongated body with an angled tab 42 to facilitate insertion of the cartridge in channel 16 of clip applier 10.

As best illustrated in FIG. 4, cartridge 40 may be constructed as a sandwich of a top cover 50 and a clip carrier 60. Clip carrier 60, for reasons described below, does not extend the full length of top cover 50 in the proximal direction. A sandwich construction may be used so as to confine and allow for movement within the cartridge of the array of clips and other elements to be described below. The cartridge sandwich elements may be held together by a conventional means such as an adhesive.

There is a slot 52 at the distal end of cartridge top cover 50 and a corresponding slot 62 at the distal end of clip carrier 60. These slots correspond to the slot 32 in clip applier 10 and enable the body tissue to be positioned so that a surgical clip may be applied.

Block 54 is attached to the proximal portion of cartridge top cover 50 by means of pins 56. Block 54 is spaced from the proximal end of clip carrier 60. This creates a slot 58 in which force-transmitting portion 34 of trigger 22 is received.

Clip carrier 60 includes a proximal member 64 and two laterally spaced cam follower members 66 which are pivotally or hingedly mounted adjacent the distal end of the proximal member. The laterally spaced cam follower members 66 are resiliently urged apart. In a preferred embodiment, this is accomplished, at least in part, by a flexural hinge 68 between each of the cam follower members 66 and the proximal member 64. During the closing of a surgical clip, the cam follower members are forced to pivot toward one another. Once the clip closure is complete, a clip carrier return spring 70 may be used to help restore the cam follower members to their original laterally spaced apart position. The ends of spring 70 are attached to the distal portions 72 of cam follower members 66. These distal portions protrude above the longitudinal plane of clip carrier 60 for a reason described below.

Located between cartridge top cover 50 and clip carrier 60 in the cartridge sandwich is a supply of surgical clips 82, 84, etc. Although cartridge 40 could contain only a single clip, it is preferable to provide a plurality of clips in a longitudinal array 80. Clip array 80 is parallel to the longitudinal axis of clip carrier 60, cartridge 40, and the longitudinal jaw 12 of clip applier 10. Each clip in the array is in contact with the immediately adjacent clips in the array. The clips are retained on a surface of clip carrier 60. The distal-most clip 82 is retained on and between the cam follower members 66 of clip carrier 60. It will be apparent to those skilled in the art that suitable surgical clips other than those illustrated in the Figures can be used in practicing the instant invention.

Cartridge top cover 50 and the proximal member 64 of clip carrier 60 contain longitudinal recesses 86 and 88, respectively, to permit longitudinal movement within the cartridge of a clip follower 90 and a clip follower spring 94. Clip follower 90 has a lug 92 which fits into recess 88 to facilitate the longitudinal movement of the clip follower. The distal surface 96 of clip follower 90 is indented to receive the rear portion of the proximal-most clip 98 in longitudinal array 80. Clip follower 90 helps to maintain proper alignment of the longitudinal clip array 80 and, as will now be described, to coact with clip follower spring 94 to advance the array of clips.

Clip follower spring 94 is a prestressed compression coil spring which acts between retainer 100 and clip follower 90. Retainer 100 is attached to cartridge top cover 50 and proximal member 64 by pin 102. This serves to fix the position of clip follower spring 94 in relation to cartridge 40.

As shown in FIGS. 5 and 6, when trigger 22 is squeezed, the force-transmitting portion 34 of the trigger moves in the distal direction. This in turn causes cartridge 40 to move in the distal direction, such that cam follower members 66 contact clip applier jaw cam surfaces 30. Further distal motion of the cartridge causes cam follower members 66 to pivot about flexural hinges 68. Cam follower members 66 move toward one another along cam surfaces 30. This causes distal-most clip 82 to be closed around the body tissue, which typically is a tubular structure 104.

The operation of clip applier 10 and cartridge 40 in carrying out a complete clip closing and return stroke cycle is illustrated by FIGS. 7–11. FIG. 7 shows the position of the distal end of the clip applier and cartridge prior to the squeezing together of the ring handles (not shown in FIG. 7). The tubular structure is placed in slots 32, 52, and 62 between the distal portions 72 of cam follower members 66. The distal-most clip 82 is ready to be closed around tubular structure 104 without the necessity for any preliminary distal motion by the distal-most clip relative to cam follower members 66.

FIG. 8 shows the condition of the apparatus once the squeezing of the ring handles has begun. Cartridge 40 has begun to move in the distal direction. Cam follower members 66 pivot toward each other by traversing jaw cam surfaces 30 through the action of the flexural hinges 68. This causes the closing of distal-most clip 82 around tubular structure 104. The distal-most clip is confined within the clip carrier during closing by a pair of proximal-facing stop surfaces 74 on the distal portions 72 of cam follower members 66. The pivoting of cam follower members 66 also causes the ends of the clip carrier return spring 70 to move toward each other.

FIG. 9 shows the condition of the apparatus at the peak of the clip-closing stroke, that is, when the ring handles are squeezed completely together. Cartridge 40 is at its distal-most position and cam follower members 66 are nearest to each other. This causes distal-most clip 82 to close completely around tubular structure 104. The ends of clip carrier return spring 70 are also nearest to each other at this point. Although not shown in FIG. 9, it would be in accordance with this invention for portions of cam follower members 66 and distal-most clip 82 to protrude beyond the distal end of the longitudinal jaw 12 of clip applier 10.

Figure 10:
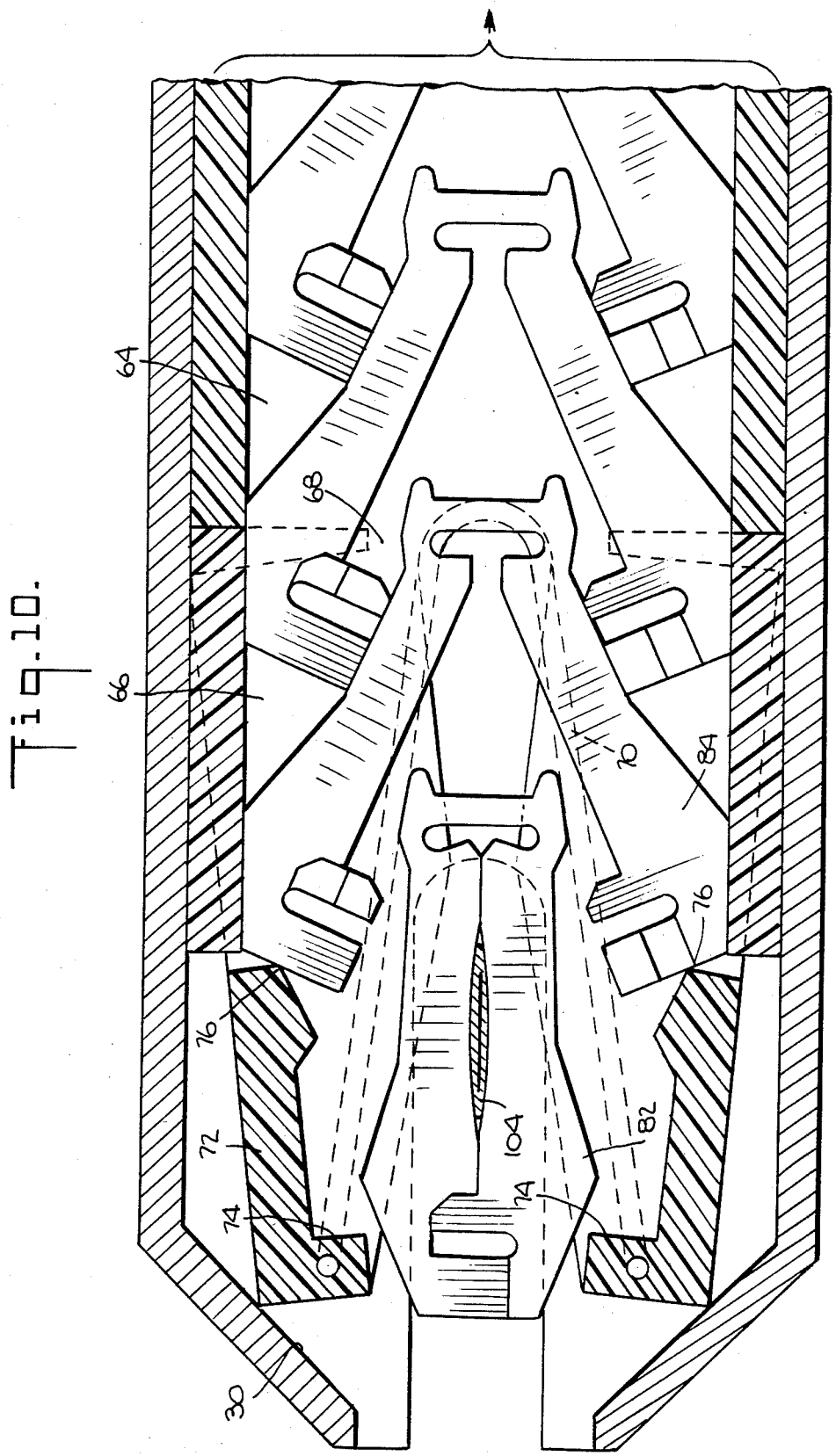
FIG. 10 is a view similar to FIG. 7 except that an intermediate retraction from the peak clip-closing position is shown.

FIG. 10 shows the condition of the apparatus once the return stroke has begun. The operator allows the ring handles to start to return to their original separated positions. The return of trigger 22 causes force-transmitting portion 34, and thus cartridge 40, to move in the proximal direction. Cam follower members 66 now separate by re-traversing cam surfaces 30 in the proximal direction as flexural hinges 68 pivot. Separation of cam follower members 66 is assisted by clip carrier return spring 70. At this point, the closed distal-most clip clears proximal-facing stop surfaces 74. As distal-most clip 82 loses contact with clip carrier 60, clip follower spring 94 urges clip follower 90 in the distal direction, thereby advancing the array of clips. The next-to-distal-most clip 84 is prevented from prematurely entering the space between cam follower members 66 by a second pair of proximal-facing stop surfaces 76 on the distal portions 72 of cam follower members 66.

FIG. 11 shows the condition of the apparatus when the return stroke is nearly complete. The ring handles, trigger, and cartridge 40 have returned to their original positions. Cam follower members 66 are no longer in contact with cam surfaces 30. This enables the next-to-distal most clip 84 to move past the second pair of stop surfaces 76 and to begin to move toward stop surfaces 74. The continued action of clip follower 90 and clip follower spring 94 will move clip 84 into position against stop surfaces 74 (comparable to the initial position of clip 82 as shown in FIG. 7).

Clip applier 10 may now simply be withdrawn from tubular structure 104, which has been closed by the deformation of distal-most clip 82. Clip applier 10 is now ready to be used to apply the next clip 84 to another tubular structure. This procedure can be repeated until the supply of clips in cartridge 40 has been exhausted. Cartridge 40 is then removed from clip applier 10 and thrown away. Another cartridge 40 with a supply of clips may then be inserted in clip applier 10 to perform another series of clip closures.

It will be understood that the foregoing is only illustrative of the principles of the invention, and that various modifications can be made by those skilled in the art without departing from the scope and spirit of the invention.

What is claimed is:

1. Apparatus for applying a surgical clip to body tissue comprising:
    a longitudinal shaft having a distal portion including two laterally spaced, relatively fixed cam surface portions which are inclined toward one another in the distal direction;
    clip carrier means for both carrying and closing a surgical clip mounted for longitudinal reciprocal motion relative to the shaft and including a proximal member and two laterally spaced cam follower members pivotally mounted adjacent the distal end of the proximal member, the cam follower members being initially located proximally of the cam surface portions and having surface portions for engaging and supporting a surgical clip in the space between the cam follower members; and
    means for causing the clip carrier means to move distally relative to the shaft so that each of the cam follower members engages a respective one of the cam surface portions to force the cam follower members toward one another and close the surgical clip.

2. The apparatus defined in claim 1 wherein the distal portion of the shaft includes a slot between the cam surface portions for admitting the tissue to be clipped between the cam surface portions.

3. The apparatus defined in claim 1 further comprising means for resiliently urging the cam follower members apart.

4. The apparatus defined in claim 3 wherein the means for resiliently urging the cam follower members apart includes a flexural hinge between each of the cam follower members and the proximal member.

5. The apparatus defined in claim 3 wherein the means for resiliently urging the cam follower members apart includes spring means acting between the cam follower members.

6. The apparatus defined in claim 3 further comprising means for urging the clip in the distal direction relative to the cam follower members.

7. The apparatus defined in claim 6 wherein the clip engaging surface portions include proximal-facing stop surfaces for stopping distal motion of the clip relative to the cam follower members before the cam follower members engage the cam surface portions to close the clip.

8. The apparatus defined in claim 7 wherein the clip carrier means contains a plurality of clips in a longitudinal array parallel to the longitudinal axis of the shaft, each clip in the array being in contact with the immediately adjacent clips in the array, but only the distal-most clip in the array being disposed between the cam follower members, and wherein the apparatus includes means for urging all of the clips in the array in the distal direction relative to the cam follower means so that, after each clip is closed and the cam folower members return to their initial positions, the next distal-most clip in the array enters the space between the cam follower members.

9. The apparatus defined in claim 8 wherein the clip engaging surface portions include second proximal-facing stop surfaces for preventing the next-to-distal-most clip in the array from entering the space between the cam follower members while the cam follower members are in engagement with the cam surface portions.

10. A replaceable cartridge for use with a surgical instrument for applying surgical clips to body tissue, the instrument including a longitudinal jaw member having proximal and distal end portions with a pair of laterally spaced, relatively fixed jaws mounted on the distal end of the jaw member, each jaw having a camming surface which converges in the distal direction toward the camming surface of the other jaw, and means for causing the cartridge to move distally relative to the instrument, the cartridge comprising:
- a carrier for both carrying and closing a linear array of clips, including a proximal member and two laterally spaced cam follower members pivotally mounted adjacent the distal end of the proximal member, the cam follower members being initially located proximally of the instrument jaw camming surfaces;
- first clip carrier stop surfaces for confining the distal-most clip within the clip carrier while the distal-most clip is closed; and
- second clip carrier stop surfaces for retarding the distal motion of the next-to-distal-most clip while the distal-most clip is closed;
- wherein each of the clip carrier cam follower members is reciprocally hinge pivotable and traverses one of the instrument jaw camming surfaces to force the cam follower members toward one another to close the distal-most clip when the cartridge is moved distally relative to the instrument.

11. The cartridge defined in claim 10 wherein the clip carrier is positioned so as to apply the distal-most clip to body tissue without the necessity for preliminary distal motion of the distal-most clip.

12. The cartridge defined in claim 10 further comprising cam follower member return means for returning each of the pivoted cam follower members to its initial position when the distal-most clip has been closed.

13. The cartridge defined in claim 12 further comprising means for moving the cartridge relative to the surgical instrument in the proximal direction to permit the application of the succeeding clip after the cartridge has been moved in the distal direction to close a clip.

14. The cartridge defined in claim 12 further comprising clip follower means for aligning the proximal-most clip in the linear array with the cartridge.

15. The cartridge defined in claim 14 further comprising spring means for resiliently urging the clip follower means in the distal direction within the cartridge.

16. The cartridge defined in claim 12 wherein the cam follower member return means is a spring which is connected to the distal portions of the cam follower members.

17. The cartridge defined in claim 16 wherein the distal portions of the cam follower members protrude above the longitudinal plane of the clip carrier.

18. A cartridge removably mountable in a surgical clip applying instrument comprising:
- a longitudinal member having proximal and distal ends for both carrying and closing a plurality of surgical clips;
- two laterally spaced cam follower members pivotally mounted adjacent the distal end of the longitudinal member;
- means for resiliently urging the cam follower members apart;
- a plurality of surgical clips disposed in a longitudinal array substantially parallel to the longitudinal member; and
- means for urging all of the clips in the distal direction relative to the longitudinal member so that the distal-most clip in the array is urged into the space between the cam follower members for closing by the cam follower members when those members are forced toward one another by the clip applying instrument.

19. The apparatus defined in claim 18 wherein the longitudinal member and the cam follower members include surface portions for retaining the distal-most clip in the space between the cam follower members prior to closing of the distal-most clip.

20. The apparatus defined in claim 19 wherein the clip retaining surface portions include proximal-facing stop surfaces for stopping distal motion of the distal-most clip prior to closing of that clip.

21. The apparatus defined in claim 20 wherein the cam follower members include second proximal-facing stop surfaces for preventing the next-to-distal-most clip in the array from entering the space between the cam follower members while those members are forced toward one another by the clip applying instrument.

22. The apparatus defined in claim 18 wherein the means for resiliently urging the cam follower members apart comprises a flexural hinge between each of the cam follower members and the longitudinal member.

23. The apparatus defined in claim 18 wherein the means for resiliently urging the cam follower members apart comprises a spring acting between the cam follower members.

24. A replaceable cartridge for use with a surgical instrument for applying a plurality of surgical clips one at a time in succession to body tissue, the cartridge comprising:
- a carrier for both carrying and closing a linear array of clips, including a proximal member and two laterally spaced cam follower members pivotally mounted adjacent the distal end of the proximal member;
- a plurality of clips disposed in a longitudinal array substantially parallel to the clip carrier, so that the distal-most clip is in position to be closed without preliminary distal motion of the distal-most clip relative to the clip carrier;
- wherein the cam follower members are reciprocally hinge pivotable and moved toward each other by the surgical instrument to close the distal-most clip.

25. The cartridge defined in claim 24 further comprising first clip carrier stop surfaces for confining the distal-most clip within the cam follower members and second clip carrier stop surfaces for retarding the distal motion of the next-to-distal-most clip while the distal-most clip is being closed.

26. The cartridge defined in claim 25 wherein the first and second clip carrier stop surfaces protrude above the longitudinal plane of the cam follower members.

27. The cartridge defined in claim 24 further comprising means for returning each of the pivoted cam follower members to its initial position when the distal-most clip has been closed.

28. The cartridge defined in claim 27 wherein the cam follower member return means is a spring which is connected to the distal portions of the cam follower members.

29. The cartridge defined in claim 24 wherein the cartridge is movable relative to the surgical instrument first in the distal direction to effect the closing of the distal-most clip and then in the proximal direction to permit the application of the succeeding clip.

30. The cartridge defined in claim 29 further comprising clip follower means for aligning the proximal-most clip in the longitudinal array with the cartridge.

31. The cartridge defined in claim 30 further comprising spring means for resiliently urging the clip follower means in the distal direction within the cartridge.

* * * * *